US00PP25404P3

(12) United States Plant Patent
Korlipara

(10) Patent No.: US PP25,404 P3
(45) Date of Patent: Mar. 31, 2015

(54) ***COREOPSIS* PLANT NAMED 'IMPERIAL SUN'**

(50) Latin Name: ***Coreopsis verticillata* hybrid**
Varietal Denomination: Imperial Sun

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 180 days.

(21) Appl. No.: 13/815,534

(22) Filed: Mar. 8, 2013

(65) Prior Publication Data

US 2014/0259243 P1 Sep. 11, 2014

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Anne Grunberg
(74) *Attorney, Agent, or Firm* — Klarquist Sparkman, LLP

(57) ABSTRACT

A new and distinct *Coreopsis* plant named 'Imperial Sun' characterized by daisy-type inflorescences that grow to 4.5 cm in diameter, inflorescences that are bright yellow, plants hardy to Zone 6, maybe lower, grass green foliage on short stems, flowering for the whole summer, a low, mounding habit, and excellent vigor.

1 Drawing Sheet

Latin name: *Coreopsis verticillata* hybrid.
Varietal denomination: 'Imperial Sun'.

BACKGROUND OF THE INVENTION

The present invention relates to a new and distinct *Coreopsis* and given the cultivar name 'Imperial Sun'. *Coreopsis* is in the family Asteraceae. This new cultivar originated from a controlled breeding program to produce hardy compact *Coreopsis verticillata* types. The new cultivar originated as an F2 interspecific hybrid seedlings of proprietary unnamed parents. This new cultivar of *Coreopsis* is a herbaceous perennial to be grown for landscape and container use in a sunny site.

Compared to the parent plants, the new cultivar has a shorter and denser habit and larger flowers.

Compared to *Coreopsis verticillata* 'Zagreb', an unpatented plant, the new cultivar has larger inflorescences and a shorter habit.

SUMMARY OF THE INVENTION

The following traits have been repeatedly observed and are determined to be the unique characteristics of the new variety. These characteristics in combination distinguish *Coreopsis* 'Imperial Sun' as a new and distinct cultivar:

1. daisy-type inflorescences that grow to 4.5 cm in diameter,
2. inflorescences that are bright yellow,
3. plants hardy to Zone 6, maybe lower,
4. grass green foliage on short stems,
5. flowering for the whole summer,
6. a low, mounding habit, and
7. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a nine-month-old *Coreopsis* 'Imperial Sun' growing in a one-gallon container in full sun in August in Canby, Oreg.

DETAILED PLANT DESCRIPTION

The following is a detailed description of the new *Coreopsis* cultivar based on observations of ten-month-old specimens growing in one-gallon containers in full sun in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zones 6 to 9.
*Size*.—45 cm wide and 33 cm tall to top of inflorescences.
*Form*.—Mound.
*Vigor*.—Excellent.
*Roots*.—Fibrous, stems root easily from stem cuttings.

Stem:

*Type*.—Ascending, well branched.
*Size*.—Grows to 20 cm tall to where branches for flowering and 8 mm wide.

*Number of stems from the crown.*—6.

*Branching habit.*—Freely branched, with secondary branches, branches are opposite in arrangement, new lateral flowering branches are continuously produced throughout the summer.

*Internode length.*—0.7 cm to 4 cm.

*Surface.*—Minutely glandular.

*Color.*—Grey Brown N199A at bottom 5 cm blending to Green 137A.

Leaf:

*Type.*—Simple.

*Shape.*—Pinnately parted to linear with thread-like segments.

*Arrangement.*—Opposite.

*Size.*—Thread-like segments can spread to 12 cm wide and 8 cm long, the terminal linear segment can grow to 60 mm long and 2 mm wide, laterals can grow to 45 mm long and 2 mm wide.

*Apex.*—Acute.

*Margins.*—Entire.

*Petiole.*—0 to 5 mm long and 1 mm wide, Green N137A.

*Surface texture.*—Glabrous on both sides.

*Venation.*—Pinnate, visible main vein the same color as the leaf on both sides.

*Color.*—Both sides Yellow Green 147A.

Inflorescence:

*Type.*—Long stalked terminal heads of daisy type inflorescences.

*Peduncle.*—Grows to 3.5 cm long, 1 mm wide, glabrous, Green 137A.

*Size.*—Grows to 4.5 cm wide and 7 mm deep.

*Immature.*—Globular, 5 mm wide and 6 mm deep, Yellow Green147B, glabrous.

*Receptacle.*—Disc shaped, 3 mm wide and 1.5 mm deep, Green 136D.

*Phyllaries.*—In 2 series, both reflexed; first series closet to ray florets in an area 6 mm deep and spreading 10 wide mm wide, 8 in number, each 6 mm long and 2.5 mm wide, lanceolate, margin entire, tip acute, glabrous on both sides, both sides Yellow Green N144A on top ⅓ and 147C on bottom ⅔; lower series in an area 2 mm deep and 8 mm wide, 5 linear lobes, each 3 mm long and 0.5 mm wide, margin entire, tip with hairs, top side glandular, bottom side glabrous, both sides Green 137A.

*Self-cleaning.*—Yes.

*Lastingness.*—Each inflorescence lasts about a week on the plant.

Florets:

*Type.*—Composite.

*Ray florets.*—8 in number with no pistil or stamen, grows to 25 mm long, 8 mm wide, elliptical to obovate, with the tip acute, margins entire, glabrous on both sides; topside Yellow 12A, bottom side Yellow 12B.

*Disc.*—Flat becoming rounded with maturity, 7 mm wide and becoming 5 mm deep with maturity, Greyed Purple 187A.

*Disc florets.*—Tubular, with stamen and pistil, about 40 in number, 9 mm long and 1.5 mm wide, tubular; corolla 5.5 mm long, 5 lobed, tube Yellow 12A, lobes Greyed Purple 187A; pistil 1, 6 mm long, ovary 2 mm long, Green Yellow 1B, style 4 mm long, with extruding, 2-branched stigma, style Yellow Orange 16A, stigma Orange 25A; stamen 5, anthers 2 mm long, Greyed Brown 200A, pollen Yellow 11A.

*Bloom period.*—June through frost in Canby, Oreg.

*Fragrance.*—None.

*Seed.*—None seen.

*Fertility.*—Unknown.

Disease and pests: No pests or diseases have been observed on plants grown under commercial conditions in Canby, Oreg. No resistances are known.

I claim:

1. A new and distinct *Coreopsis* plant as herein illustrated and described.

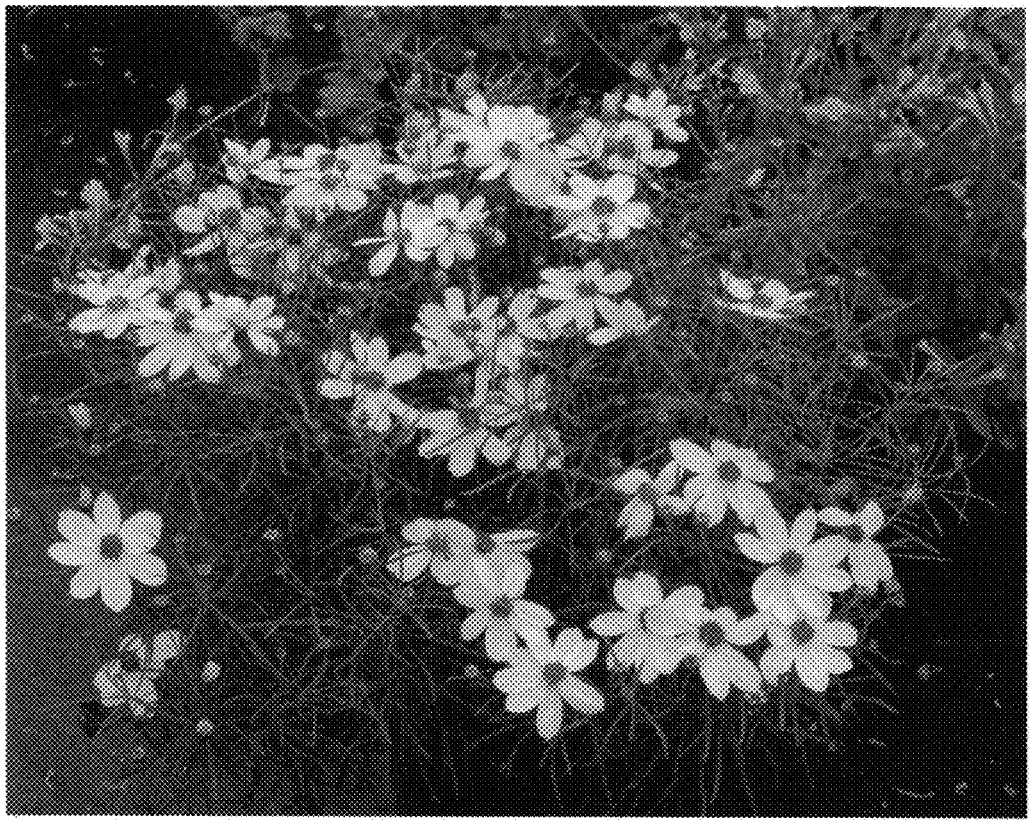

* * * * *